(12) United States Patent
Arndt et al.

(10) Patent No.: US 7,611,647 B2
(45) Date of Patent: Nov. 3, 2009

(54) PROCESS FOR THE SELECTIVE DEPROTONATION AND FUNCTIONALIZATION OF 1-FLUORO-2-SUBSTITUTED-3-CHLOROBENZENES

(75) Inventors: Kim E. Arndt, Carmel, IN (US); Mark V. M. Emonds, Midland, MI (US); James M. Renga, Indianapolis, IN (US); Jossian Oppenheimer, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 12/350,259

(22) Filed: Jan. 8, 2009

(65) Prior Publication Data
US 2009/0182168 A1    Jul. 16, 2009

Related U.S. Application Data

(60) Provisional application No. 61/010,918, filed on Jan. 11, 2008.

(51) Int. Cl.
*C07F 1/02* (2006.01)
*C07C 65/00* (2006.01)

(52) U.S. Cl. ............... 260/665 R; 562/473; 562/474
(58) Field of Classification Search ............ 260/665 R; 562/473, 474
See application file for complete search history.

(56) References Cited

U.S. PATENT DOCUMENTS 7,300,907 B2    11/2007  Epp
7,314,849 B2     1/2008  Balko
2006/0131762 A1*  6/2006  Meudt et al. ............ 260/665 R

FOREIGN PATENT DOCUMENTS

WO    2008/006627    1/2008

OTHER PUBLICATIONS

Pfeffer et al., synthesis and characterization of asymmetric C,N-cyclometallated complexesof Mo, Journal of Organometallic chemistry 494 (1995) 187-193.*

* cited by examiner

Primary Examiner—Jafar Parsa
(74) Attorney, Agent, or Firm—Craig Mixan

(57) ABSTRACT

1-Fluoro-2-substituted-3-chlorobenzenes are selectively deprotonated and functionalized in the position adjacent to the fluoro substituent.

7 Claims, No Drawings

PROCESS FOR THE SELECTIVE DEPROTONATION AND FUNCTIONALIZATION OF 1-FLUORO-2-SUBSTITUTED-3-CHLOROBENZENES

This application claims the benefit of U.S. Provisional Application Ser. No. 61/010,918 filed on Jan. 11, 2008. The present invention concerns a process for the selective deprotonation and functionalization in the position adjacent to the fluoro substituent of certain 1-fluoro-2-substituted-3-chlorobenzenes.

BACKGROUND OF THE INVENTION

U.S. Pat. Nos. 7,314,849 and 7,300,907 describe respectively certain 6-(poly-substituted aryl)-4-aminopicolinate and 2-(poly-substituted aryl)-6-amino-4-pyrimidinecarboxylic acid compounds and their use as herbicides. 2-Fluoro-3-substituted-4-chlorophenylboronic acid derivatives are useful intermediates for the preparation of these herbicides.

In U.S. Pat. Nos. 7,314,849 and 7,300,907, for instance, 2-fluoro-3-substituted-4-chlorophenyl-boronic acids derivatives are prepared by halogen-metal exchange of 1-bromo-2-fluoro-3-substituted-4-chlorobenzenes with n-butyl lithium followed by quenching with a boronic acid ester.

It would be advantageous to produce these materials by direct deprotonation rather than by halogen-metal exchange. This allows the use, for instance, of less complex starting materials and avoids the formation of a brominated waste stream.

SUMMARY OF THE INVENTION

The present invention concerns the highly selective deprotonation of 1-fluoro-2-substituted-3-chlorobenzenes in the position adjacent to the fluoro substituent with alkyl lithium compounds. The resulting lithiobenzenes are further derivatized or functionalized by reaction with electrophilic reagents. More particularly, the present invention concerns a process for the preparation of a lithiobenzene of Formula I

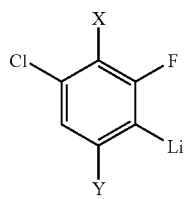

wherein
X represents F, $OR^1$ or $NR^2R^3$;
Y represents H or F; and
$R^1$, $R^2$ and $R^3$ independently represents a $C_1$-$C_4$ alkyl group;

which comprises contacting a substituted fluorobenzene of Formula II

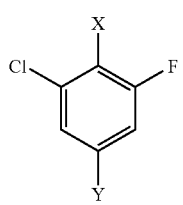

wherein X, Y, $R^1$, $R^2$ and $R^3$ are as previously defined with an alkyl lithium in an inert organic solvent. In another aspect of the present invention, the lithiobenzenes are further contacted with an electrophilic reagent. Preferred electrophilic reagents include esters of boronic acid, carbon dioxide, N,N-dialkylformamides and alkyl formates.

DETAILED DESCRIPTION OF THE INVENTION

The term alkyl and derivative terms such as alkoxy, as used herein, include straight chain, branched chain and cyclic groups. Thus, typical alkyl groups are methyl, ethyl, 1-methylethyl, propyl, cyclopropyl, butyl, 1,1-dimethylethyl, cyclobutyl and 1-methylpropyl. Methyl and ethyl are often preferred. Alkyl groups are sometimes referred to as normal (n), iso (i), secondary (s), or tertiary (t).

The 1-fluoro-2-substituted-3-chlorobenzene starting materials are known compounds and can be prepared by procedures well known to those skilled in the art.

Selective deprotonation in the position adjacent to the fluoro substituent is achieved by contacting the 1-fluoro-2-substituted-3-chlorobenzene starting material with an alkyl lithium in an inert organic solvent.

The alkyl lithium compound serves as a strong base. Any alkyl lithium compound can be employed; commercially available alkyl lithium compounds like methyl lithium, n-butyl lithium and s-butyl lithium are preferred. While complete conversion would require one equivalent of the alkyl lithium base, it is often more beneficial to conduct the reaction with a slight excess of the alkyl lithium. Typically about a 1 to about a 10 percent molar excess of alkyl lithium is preferred with about a 2 to about a 5 percent molar excess being more preferred.

The reaction is conducted under anhydrous conditions in an inert organic solvent, i.e., an organic material in which the reactants are at least partially soluble and which is chemically inert to the reactants. By being chemically inert to the reactants is meant that the solvent is at least less reactive than the 1-fluoro-2-substituted-3-chlorobenzenes are to the strong alkyl lithium base. Suitable inert organic solvents include $C_5$-$C_8$ straight-chain, branched or cyclic hydrocarbons, such as pentanes, hexanes, cyclohexane and iso-octane, and ethers, such as diethyl ether, tetrahydrofuran, dioxane and glycol ethers. Ethers are generally preferred. Mixtures of hydrocarbons and ethers are often preferred, with mixtures of tetrahydrofuran or 1,2-dimethoxyethane and commercial mixtures of octanes being most preferred. The deprotonation is conducted at a temperature from about −100° C. to about 0° C. depending upon the nature of the substituent X, the solvent and the alkyl lithium employed. The optimal temperature can be readily determined by routine optimization. For example, when X is F or Cl the preferred temperature for deprotonation is from about −100° C. to about −50° C. When X is $OR^1$ or $NR^2R^3$, the preferred temperature for deprotonation is from about −70° C. to about −50° C.

The process is not sensitive to pressure and is usually carried out at or slightly above atmospheric pressure. The process is preferably conducted under a dry inert atmosphere such as that provided by a nitrogen blanket.

The lithiobenzenes of Formula I are not typically isolated but, are reacted with an electrophilic reagent. An electrophilic reagent is defined as a reagent that seeks a pair of electrons. Suitable electrophilic reagents include but are not limited to bromine, iodine, sulfur, disulfides, sulfur dioxide, boronic acid esters, carbon dioxide, sulfuryl halides, phosphoryl halides, aldehydes, amides and alkyl or acyl halides. Boronic acid esters, carbon dioxide, N,N-dialkyl-formamides and alkyl formates are particularly preferred electrophilic reagents. The lithiobenzene reaction mixture can be cooled and the electrophilic reagent added to the reaction solution. Alternatively, the lithiobenzene can be added to the electrophilic reagent at about −70° C. to about −50° C. when X represents $OR^1$ or $NR^2R^3$ and at −100° C. to −60° C. when X represents F or Cl. The final product, whose properties will depend upon the nature of the electrophilic reagent, can be isolated and recovered by conventional procedures well known to those skilled in the art.

In a typical reaction, a 1-fluoro-2-substituted-3-chlorobenzene starting material is dissolved in a dry ethereal solvent under a nitrogen atmosphere. The reaction mixture is cooled and the alkyl lithium compound is added; the reaction mixture is allowed to stir until deprotonation is complete. The reaction mixture is again cooled and then treated with an electrophilic reagent. After the lithiobenzene is completely quenched, the reaction mixture is worked up to recover the product.

The following examples are presented to illustrate the invention.

EXAMPLES

1. Preparation of 2-(4-chloro-2-fluoro-3-methoxyphenyl)-[1,3,2]-dioxaborinane

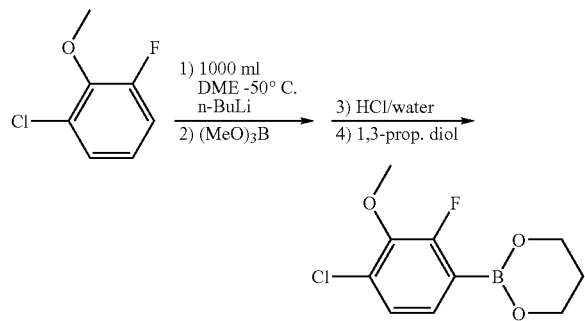

To a solution of 2-chloro-6-fluoroanisole (100 g) in 1 liter (L) of dry 1,2-dimethoxyethane (DME), cooled to −70° C., was added 274 milliliters (mL) of 2.5 M n-BuLi in hexane over 12 minutes (min) with good magnetic stirring. During the addition the reaction warmed to −58° C. The dry ice bath was removed and the reaction allowed to warm to −50° C. for 20 min to allow a small amount of a white solid to dissolve. A small sample was drawn up directly into a 1 mL syringe containing 0.15 mL of MeSSMe. The sample was diluted with ether and extracted with water. The organic phase was checked by GC. Only 4% starting material was present in the scan.

The solution was cooled to −70° C., before adding 74.4 grams (g) of trimethyl borate, dropwise. The addition took about 15 min and the temperature was held below −45° C. The colorless solution was warmed to 0° C. with a warm water bath before 140 g of 37% aq. HCl was added nearly at once. The near colorless solution gave off a gas and reached 27° C. and was stirred for 20 min before transferring the two phase mixture to a separatory funnel. The lower viscous water layer (285 mL) was separated and reserved. The organic phase was placed in a 2 L roto-vap flask and 62 g of 1,3-propanediol was added to the cloudy colorless solution. The reserved water layer was extracted once with 300 mL of ether and the phases were separated into 195 mL of the aqueous fraction and about 390 mL of organic phase. The organic phase was added into the 2 L roto-vap flask. This cloudy solution was concentrated and warmed to 60-70° C. to give an near colorless oil with some water present. The mixture was taken into 700 mL of methylene chloride, dried with $MgSO_4$, filtered and concentrated to 156 g of a colorless oil. $^1H$ NMR and GC indicated about 5% by weight of excess propanediol.

The oil was heated on the Kugelrohr at 10-12 mm Hg vacuum to 160° C. for ten minutes. Some light material came over and the sample weighed 152 g. GC showed a 2% improvement in purity to 94.2%. $^1H$ NMR ($CDCl_3$, 300 MHz): δ 7.15 (dd, 1H, J=6.0, 8.3 Hz,), 6.95 (dd, 1H, J=1.3, 8.3 Hz), 4.05 (t, 4H, J=5.7), 3.8 (s, 3H), 1.95 (m, 2H, J=5.7 Hz).

2. Preparation of 4-chloro-2-fluoro-3-methoxyphenylboronic acid

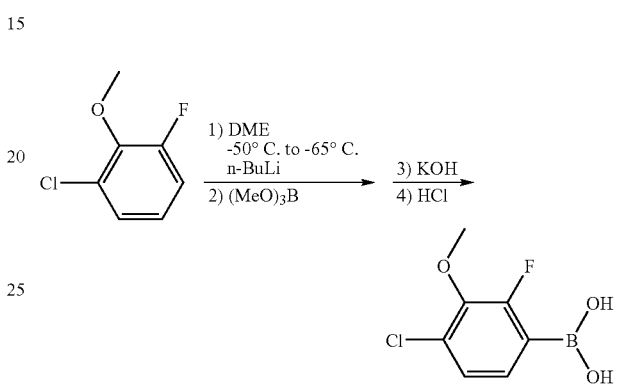

A solution of 2-chloro-6-fluoroanisole (40.2 g) in anhydrous 1,2-dimethoxyethane (313 mL) was prepared in a 1-liter three-necked flask equipped with a magnetic stirrer, thermowell with thermocouple temperature probe, a rubber septum, and a condenser with a nitrogen pad. The solution was stirred and cooled to −69.6° C. using a dry ice/acetone bath. A solution of butyllithium (115 mL of 2.5 M butyllithium in hexanes) was added slowly over 4.15 hours using a syringe pump, maintaining the reaction temperature below −65° C. The reaction mixture was stirred for 20 minutes at −70.3° C. to −72.6° C., then trimethyl borate (43 mL) was added slowly over 1.6 hours using a syringe pump, maintaining temperature below −65° C. Upon completion of the trimethyl borate addition, the reaction mixture was allowed to slowly warm to ambient temperature overnight.

A solution of potassium hydroxide in water (69.2 g of 45% KOH solution diluted with 485 mL of deionized water) was added to the reaction mixture (at ambient temperature=23.3° C.) over 26 minutes using an addition funnel. The mixture was stirred for 60 minutes, and then it was transferred to a separatory funnel where the phases were allowed to separate. The aqueous layer was washed with tert-butyl methyl ether (2×305 mL) to remove unreacted 2-chloro-6-fluoroanisole. The aqueous layer was then transferred to a 1-liter Erlenmeyer flask and acidified by the dropwise addition of 6 M aqueous hydrochloric acid (161 mL). The mixture first turns milky, then the bulk of the product separates as a yellow oil. The product was extracted from the acidified mixture using ethyl acetate (2×304 mL). The ethyl acetate layers were combined, washed with saturated aqueous sodium chloride (304 mL), dried with anhydrous magnesium sulfate, filtered, and concentrated on a rotary evaporator to obtain a white solid. The solid product was dried in vacuo overnight at ambient temperature to obtain 45.1 g of 4-chloro-2-fluoro-3-methoxyphenylboronic acid (88.3% yield); MP. 233-234° C.; $^1H$ NMR ($CD_3CN$, 300 MHz) δ 3.92 (d, 3H, $J_{HF}$=1.2 Hz), 6.25 (br s, 2H), 7.23 (dd, 1H, J=8.1, 1.5 Hz), 7.35 (dd, 1H, J=8.1, 6.2 Hz) ppm.

3. Alternate Preparation of 4-chloro-2-fluoro-3-methoxyphenylboronic acid solution in acetonitrile

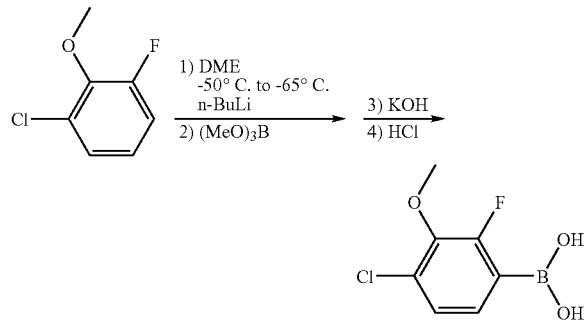

A solution of 2-chloro-6-fluoroanisole (9.6 g) in anhydrous 1,2-dimethoxyethane (75 mL) was prepared in a 100-mL three-necked flask equipped with a magnetic stirrer, thermowell with thermocouple temperature probe, a rubber septum, and a condenser with a nitrogen pad. The solution was stirred and cooled to −71.0° C. using a dry ice/acetone bath. A solution of butyllithium (31.5 mL of 2.5 M butyllithium in hexanes) was added slowly over 1.57 hours using a syringe pump, maintaining the reaction temperature below −65° C. The reaction mixture was stirred for 20 minutes at −72.0° C. to −73.4° C., then trimethyl borate (10.5 mL) was added slowly over 43 minutes using a syringe pump, maintaining temperature below −65° C. Upon completion of the trimethyl borate addition, the reaction mixture was allowed to slowly warm to ambient temperature overnight.

A solution of potassium hydroxide in water (133 mL of 5.6% aqueous potassium hydroxide, approximately 1 M) was added to the reaction mixture (at ambient temperature=23.1° C.) over 17 minutes using an addition funnel. The mixture was stirred for 60 minutes, and then it was transferred to a separatory funnel where the phases were allowed to separate. The aqueous layer was washed with tert-butyl methyl ether (2×73 mL) to remove unreacted 2-chloro-6-fluoroanisole. The aqueous layer was then transferred to a 250-mL Erlenmeyer flask, diluted with acetonitrile (76 mL), and acidified by the dropwise addition of 6 M aqueous hydrochloric acid (40 mL). The organic layer (27.87 g) was separated and found to contain 5.00 g of the product 4-chloro-2-fluoro-3-methoxyphenylboronic acid by gas chromatographic assay. The aqueous layer was extracted with additional acetonitrile (2×76 mL) and the two additional organic layers (24.88 g and 156.48 g) were likewise assayed. The total recovered product in acetonitrile solution was 9.85 g (80.3% yield).

4. Preparation of 4-chloro-2-fluoro-3-methoxybenzoic acid

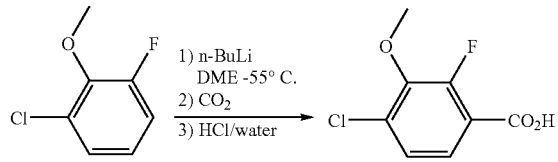

To a magnetically stirred solution of 2-chloro-6-fluoroanisole (16.06 g) in 100 mL of anhydrous DME, cooled to −70° C., was added 44 mL of 2.5 M n-BuLi in hexanes over 30 min, while keeping the reaction temperature below −55° C. After stirring the reaction for an additional 60 min at −70° C., dry carbon dioxide was bubbled into the reaction mixture for 60 min, while keeping the temperature below −60° C. Upon warming to room temperature, the reaction mixture was added to 150 mL of ether and acidified with 37% aq. HCl. The aqueous layer was washed with 2×150 mL of ether, and the combined organic layers were washed with sat. NaCl and were dried ($Mg_2SO_4$). Solvent removal gave 20.3 g of a white solid, which was recrystallized from ether/hexane to give 16.4 g (80% yield) of 4-chloro-2-fluoro-3-methoxybenzoic acid; MP 183-184° C.; $^1$H NMR ($d_6$-DMSO, 300 MHz) δ 13.5 (brs, 1H), 7.60 (dd, 1H, J=1.8, 8.8 Hz), 7.42 (dd, 1H, J=1.8, 8.8 Hz), 3.95 (s, 3H).

5. Preparation of 4-chloro-2-fluoro-3-methoxybenzaldehyde

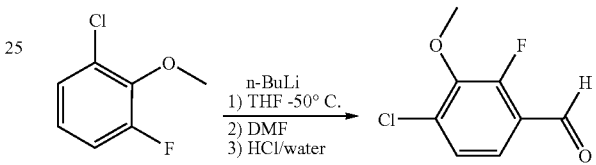

To a solution of 2-chloro-6-fluoroanisole (321.2 g) in 2 L of dry tetrahydrofuran (THF), cooled to −70° C., was added 890 mL of 2.5 M n-BuLi in hexane over 30 min with good mechanical stirring. During the addition the reaction warmed to −48 to −50° C. and was held there for 15 min after addition was complete. The solution was cooled to −75° C. before a solution of 177 g of dimethylformamide (DMF) in 100 mL of THF was added keeping the temperature below −50° C. The reaction was warmed to room temperature and 260 g of 37% aqueous HCl was slowly added and stirring was continued for 2 hours. The phases were separated and the organic phase concentrated and taken into 2 L of ether. The solution was washed twice with 500 mL of aqueous 10% HCl. The organic phase was dried over $MgSO_4$, filtered and concentrated to 372 g of a light gold oil (93% pure by GC). This oil was distilled bulb to bulb to give 282 g (75% yield) of a light gold oil that solidified upon standing. A small sample was crystallized from pentane to give fine white needles; MP 44-45° C.; $^1$H NMR ($CDCl_3$, 300 MHz) δ 10.3 (s, 1H); 7.5 (dd, 1H, J=6.6, 8.5 Hz); 7.3 (m, 1H); 4.0 (s, 3H).

What is claimed is:

1. A process for the preparation of a lithiobenzene of Formula I

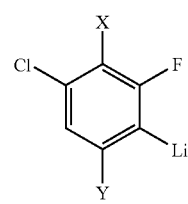

wherein
X represents F, $OR^1$ or $NR^2R^3$;
Y represents H or F; and $R^1$, $R^2$ and $R^3$ independently represents a $C_1$-$C_4$ alkyl group;

which comprises contacting a substituted fluorobenzene of Formula II

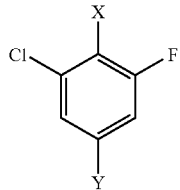

II wherein X, Y, $R^1$, $R^2$ and $R^3$ are as previously defined with an alkyl lithium in an inert organic solvent.

2. The process of claim 1 in which the alkyl lithium is n-butyl lithium.

3. The process of claim 1 in which the inert organic solvent is an hydrocarbon, an ether or mixtures thereof.

4. The process of claim 1 in which X represents $OR^1$.

5. The process of claim 1 in which the reaction mixture is further contacted with an electrophilic reagent.

6. The process of claim 5 in which the electrophilic reagent is boronic acid esters, carbon dioxide, N,N-dialkylformamides or alkyl formates.

7. A compound of the formula

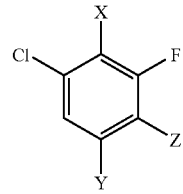

wherein

X represents $OR^1$ or $NR^2R^3$;

Y represents H or F;

Z represents —$CO_2$; and $R^1$, $R^2$ and $R^3$ independently represents a $C_1$-$C_4$ alkyl group.

\* \* \* \* \*